US008258100B2

(12) United States Patent
Enright et al.

(10) Patent No.: US 8,258,100 B2
(45) Date of Patent: *Sep. 4, 2012

(54) LIGAND/LYTIC PEPTIDE METHODS OF USE

(75) Inventors: Frederick M. Enright, Baton Rouge, LA (US); Jesse M. Jaynes, Raleigh, NC (US); William Hansel, Baton Rouge, LA (US); Kenneth L. Koonce, Baton Rouge, LA (US); Samuel M. McCann, Baton Rouge, LA (US); Wen H. Yu, Baton Rouge, LA (US); Patricia A. Melrose, Baton Rouge, LA (US); Lane D. Foil, Baton Rouge, LA (US); Philip H. Elzer, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 54 days.

This patent is subject to a terminal disclaimer.

(21) Appl. No.: 12/488,353

(22) Filed: Jun. 19, 2009

(65) Prior Publication Data

US 2010/0016227 A1    Jan. 21, 2010

Related U.S. Application Data

(60) Division of application No. 10/617,561, filed on Jul. 11, 2003, now Pat. No. 7,566,777, which is a continuation of application No. 09/381,879, filed as application No. PCT/US98/06114 on Mar. 27, 1998, now Pat. No. 6,635,740.

(60) Provisional application No. 60/041,009, filed on Mar. 27, 1997, provisional application No. 60/092,112, filed on Jun. 4, 1997, provisional application No. 60/057,456, filed on Sep. 3, 1997.

(51) Int. Cl.
*A61K 38/00* (2006.01)
*A61K 38/25* (2006.01)

(52) U.S. Cl. ........ 514/19.3; 514/9.7; 514/9.9; 514/10.1; 514/10.2; 514/10.3; 514/11.1; 514/19.4; 514/19.5; 514/21.3

(58) Field of Classification Search ................. None
See application file for complete search history.

(56) References Cited

U.S. PATENT DOCUMENTS

| 5,208,020 | A  | * | 5/1993  | Chari et al.     | ........... | 424/181.1 |
| 6,635,740 | B1 | * | 10/2003 | Enright et al.   | ........... | 530/324   |

OTHER PUBLICATIONS

Leuschner, 2003(1), The Prostate, vol. 56, pp. 239-249.*
Leuschner, 2003(2), Breast Cancer Research and Treatment, vol. 78, pp. 17-27.*

* cited by examiner

*Primary Examiner* — Robert Landsman
*Assistant Examiner* — Ian Dang
(74) *Attorney, Agent, or Firm* — Pillsbury Winthrop Shaw Pittman LLP

(57) ABSTRACT

Amphipathic lytic peptides are ideally suited to use in a ligand/cytotoxin combination to specifically inhibit cells that are driven by or are dependent upon a specific ligand interaction; for example, to induce sterility or long-term contraception, or to attack tumor cells, or to selectively lyse virally-infected cells, or to attack lymphocytes responsible for autoimmune diseases. The peptides act directly on cell membranes, and need not be internalized. Administering a combination of gonadotropin-releasing hormone (GnRH) (or a GnRH agonist) and a membrane-active lytic peptide produces long-term contraception or sterilization in animals in vivo. Administering in vivo a combination of a ligand and a membrane-active lytic peptide kills cells with a receptor for the ligand. The compounds are relatively small, and are not antigenic. Lysis of gonadotropes has been observed to be very rapid (on the order of ten minutes.) Lysis of tumor cells is rapid. The two components—the ligand and the lytic peptide—may optionally be administered as a fusion peptide, or they may be administered separately, with the ligand administered slightly before the lytic peptide, to activate cells with receptors for the ligand, and thereby make those cells susceptible to lysis by the lytic peptide. The compounds may be used in gene therapy to treat malignant or non-malignant tumors, and other diseases caused by clones or populations of "normal" host cells bearing specific receptors (such as lymphocytes), because genes encoding a lytic peptide or encoding a lytic peptide/peptide hormone fusion may readily be inserted into hematopoietic stem cells or myeloid precursor cells.

19 Claims, No Drawings

LIGAND/LYTIC PEPTIDE METHODS OF USE

RELATED APPLICATIONS

This application is a divisional of application Ser. No. 10/617,561, filed Jul. 11, 2003 now U.S. Pat. No. 7,566,777, which is a continuation of application Ser. No. 09/381,879, filed Sep. 24, 1999 (now U.S. Pat. No. 6,635,740), which is a national phase application of international application no. PCT/US98/06114, filed Mar. 27, 1998, which claims priority to provisional application Ser. No. 60/041,009, filed Mar. 27, 1997; application Ser. No. 09/869,153, filed Jun. 4, 1997 now converted to provisional application Ser. No. 60/092,112, and provisional application Ser. No. 60/057,456, filed Sep. 3, 1997. All of the foregoing applications identified in this paragraph are incorporated herein by reference in their entirety.

TECHNICAL FIELD

This invention pertains to compositions and methods for specifically inhibiting cells that are driven by or are dependent on specific ligand interactions. Examples are compositions and methods for long-term contraception or sterilization; compositions and methods for inhibiting or killing malignant and non-malignant, hormone-dependent tumors; compositions and methods for selectively killing virally infected cells; and compositions and methods for selectively destroying lymphocytes responsible for autoimmune disorders.

BACKGROUND ART

Compositions that have sometimes been used for long-term contraception include those based upon natural or synthetic steroidal hormones to "trick" the female reproductive tract into a "false pregnancy." These steroidal hormones must be administered repeatedly to prevent completion of the estrous cycle and conception. Steroids have side effects that can be potentially dangerous.

P. Olson et al., "Endocrine Regulation of the Corpus Luteum of the Bitch as a Potential Target for Altering Fertility," *J. Reprod. Fert. Suppl.*, vol. 39, pp. 27-40 (1989) discusses the luteal phase and its regulation in bitches. The following discussion appears at page 37: "Specific toxins can be linked to an antibody or hormone and carried to a specific target cell (or cells) which is then killed by the toxin. The idea of developing a 'magic bullet' has been discussed for decades but is now gaining renewed recognition as a potential, highly selective method for destroying specific tissues while leaving other tissues unharmed. For many years it was impossible to develop large quantities of antibodies which would react specifically with only single antigenic determinants. However, with the advent of monoclonal antibodies, this problem has been largely overcome. Antibodies can be developed to specific hormone receptors (such as the LH receptor) and then coupled to a toxin. All cells with LH receptors should then be destroyed. Although various cell types have not been characterized in dog corpora lutea, destruction of any luteal cell type could potentially result in luteolysis if cell types communicate." (citations omitted)

P. Olson et al., "New Developments in Small Animal Population Control," *JAVMA*, vol. 202, pp. 904-909 (1993) gives an overview of methods for preventing or terminating unwanted pregnancies in small animals. The following discussion appears at page 905: *"Tissue-specific cytotoxins—* Permanent contraception in females and males might be achieved by administration of a cytotoxin that is linked to gonadotropin-releasing hormone (GnRH) and that selectively destroys gonadotropin-secreting pituitary cells. Similarly, a cytotoxin linked to antibodies against gonadotropin receptors could be targeted to alter gonadal function. Toxins would need to be carefully targeted to specific cells, yet be safe for all other body tissues." (citation omitted).

T. Janaky et al., "Short Chain Analogs of Luteinizing Hormone-Releasing Hormone Containing Cytotoxic Moieties," *Proc. Natl. Acad. Sci. USA*, vol. 89, pp. 10203-10207 (1992) discloses the use of certain hexapeptide and heptapeptide analogs of GnRH as carriers for certain alkylating nitrogen mustards, certain anthraquinone derivatives, antimetabolite, and cisplatin-like platinum complex. The authors reported that several of the compounds exerted some cytotoxic effects on the MCF-7 breast cancer cell line.

D. Fitzgerald et al., "Targeted Toxin Therapy for the Treatment of Cancer," *J. Natl. Cancer Inst.*, vol. 81, pp. 1455-1463 (1989), reviewed targeted toxin therapies for cancers, including conjugating toxins such as *Pseudomonas* exotoxin, diphtheria toxin, and ricin to a cell-binding protein such as a monoclonal antibody or a growth factor. The conjugates are then internalized into cytoplasm, where the toxin disrupts cellular activity.

Conventional targeted toxin therapies have several drawbacks. There is a small window for treatment with a particular targeted toxin (on the order of two weeks) before the recipients immune system mounts an antibody response to the targeted toxin. These antibodies will neutralize the toxin; or worse, may result in deposition of the toxin in reticuloendothelial tissues (e.g., liver, spleen, lymph nodes, lungs, bone marrow), where they may damage otherwise healthy tissue. Aside from this drawback, the toxin must be internalized by the targeted cell and translocated into the cytoplasm to have effect.

A related approach is to link a monoclonal antibody to an enzyme. This conjugate is directed specifically to a tumor cell surface antigen. A prodrug is then administered to the patient. The prodrug is substantially less toxic than the drug that results from activation of the drug at the tumor site by the conjugated enzyme. The activated drug then selectively attacks tumor cells. See, e.g., D. Kerr et al., "Regressions and Cures of Melanoma Xenografts following Treatment with Monoclonal Antibody β-Lactamase Conjugates in Combination with Anticancer Prodrugs," *Cancer Research*, vol. 55, pp. 3558-3563 (1995); and H. Svensson et al., "In vitro and In Vivo Activities of a Doxorubicin Prodrug in Combination with Monoclonal Antibody β-Lactamase Conjugates," *Cancer Research*, vol. 55, pp. 2357-2365 (1995).

S. Sealfon et al., "Molecular mechanisms of ligand interaction with the gonadotropin-releasing hormone receptor," *Endocrine Reviews*, vol. 18, pp. 180-205 (1997) provides a review of research concerning the interaction between GnRH and its receptor.

F. Hu et al., "Theophylline and Melanocyte-Stimulating Hormone Effects on Gamma-Glutamyl Transpeptidase and DOPA Reactions in Cultured Melanoma Cells," *J. Investigative Dermatology*, vol. 79, pp. 57-61 (1982) disclosed that theophylline and melanocyte-stimulating hormone (MSH) both enhanced pigmentation in murine melanoma cells, apparently by different mechanisms. J. Murphy et al., "Genetic Construction, Expression, and Melanoma-Selective Cytotoxicity of a Diphtheria Toxin-Related α-Melanocyte-Stimulating Hormone Fusion Peptide," *Proc. Natl. Acad. Sci. USA*, vol. 83, pp. 8258-8262 (1986) discloses selective activity against melanoma cells in vitro by an MSH-diphtheria toxin conjugate. See also D. Bard, "An Improved Imaging Agent for Malignant Melanoma, Based on [Nle⁴, D-Phe⁷]α-Melanocyte Stimulating Hormone," *Nucl. Med. Comm.*, vol. 16, pp. 860-866 (1995).

W. Siegrist et al., "Homologous and Heterologous Regulation of α-Melanocyte-Stimulating Hormone Receptors in Human and Mouse Melanoma Cell Lines," *Cancer Research*, vol. 54, pp. 2604-2610 (1994) reports that it is well-established that human melanoma cells possess specific high affinity receptors for α-MSH. See also J. Tatro et al., "Melanotropin Receptors Demonstrated In Situ in Human Melanoma," *J. Clin. Invest.*, vol. 85, pp. 1825-1832 (1990).

P. Bacha et al., "Thyrotropin-Releasing Hormone-Diphtheria Toxin-related Polypeptide Conjugates," *J. Biol. Chem.*, vol. 258, pp. 1565-1570 (1983) discloses conjugates of thyrotropin-releasing hormone (TRH) with two diphtheria toxins; one of these conjugates caused a 50% inhibition of protein synthesis in rat $GH_3$ pituitary cells at $3\times10^{-9}$ M concentration. See also P. Bacha et al., "Organ-Specific Binding of a Thyrotropin-Releasing Hormone-Diphtheria Toxin Complex after Intravenous Administration to Rats," *Endocrinology*, vol. 113, pp. 1072-1076 (1983).

V. Chaudhary, "Activity of a Recombinant Fusion Protein between Transforming Growth Factor Type α and *Pseudomonas* toxin," *Proc. Natl. Acad. Sci. USA*, vol. 84, pp. 4538-4542 (1987) discloses that a fusion protein of a modified *Pseudomonas* toxin and transforming growth factor type a selectively kills cells expressing epidermal growth factor receptors. See also D. Cawley et al., "Epidermal Growth Factor-Toxin A Chain Conjugates: EGF-Ricin Is a Potent Toxin while EGF-Diphtheria Fragment A is Nontoxic," *Cell*, vol. 22, pp. 563-570 (1980).

E. Vitetta et al., "Redesigning Nature's Poisons to Create Anti-Tumor Reagents," *Science*, vol. 238, pp. 1098-1104 (1987) reviews the use of immunotoxins against tumors. Uses in preventing graft-versus-host reactions are also mentioned. The authors mentioned that in vivo effectiveness was less than desirable. Difficulties mentioned included accessibility of toxins in circulation to target cells; instability of the linkage of toxin to antibody; rapid clearance of the immunotoxins from circulation by the liver; response by the recipient's immune system to the toxin or to the monoclonal antibody, complicating long-term therapy; possible lack of specificity for neoplastic renewal cells; cross-reactivity with normal cells; heterogeneity of tumor cells; and shedding of surface antigens by tumor cells.

P. Trail et al., "Antigen-specific Activity of Carcinoma-reactive BR64-Doxorubicin Conjugates Evaluated in Vitro and in Human Tumor Xenograft Models," *Cancer Research*, vol. 52, pp. 5693-5700 (1992) disclose the conjugation of the anticarcinoma antibody BR64 to a doxorubicin derivative, and discuss the antitumor effects of the conjugate.

J. Olson, "Laboratory Evidence for the Hormonal Dependency of Meningiomas," *Human Reproduction*, vol. 9, supp. 1, pp. 195-201 (1994) discloses evidence that meningiomas, benign intracranial tumors, possess progesterone receptors.

S. Prigent et al., "The Type 1 (EGFR-Related) Family of Growth Factor Receptors and their Ligands," *Progress in Growth Factor Research*, vol. 4, pp. 1-24 (1992) reviews the biology of the epidermal growth factor (EGF), its receptor, and related ligands and receptors (e.g., c-erbB-2, c-erbB-3, TGFα, amphiregulin, heregulin), and their roles in normal cell proliferation and in the pathogenesis of human cancer. See also D. Davies et al., "Targeting the Epidermal Growth Factor Receptor for Therapy of Carcinomas," *Biochem. Pharm.*, vol. 51, pp. 1101-1110 (1996).

D. Morbeck et al., "A Receptor Binding Site Identified in the Region 81-95 of the β-Subunit of Human Luteinizing Hormone (LH) and chorionic gonadotropin (hCG)," *Molecular and Cellular Endocrinology*, vol. 97, pp. 173-181 (1993) disclosed a fifteen amino acid region of LH and hCG that acted as a receptor binding site. (LH and hCG are homologous hormones that produce similar effects.)

W. Theunis et al., "Luteinising Hormone, Follicle Stimulating Hormone and Gonadotropin Releasing Hormone Immunoreactivity in Two Insects: *Locusta migratoria* migratoroides R & F and *Sarcophaga bullata* (Parker)," *Invert. Reprod. and Develop.*, vol. 16, pp. 111-117 (1989) disclosed that materials immunologically related to LH, FSH, and GnRH were localized in cerebral tissue of *Locusta migratoria* and *Sarcophaga bullata*. See also P. Verhaert et al., "Substances Resembling Peptides of the Vertebrate Gonadotropin System Occur in the Central Nervous System of *Periplaneta americana* L.," *Insect Biochem.*, vol. 16, pp. 191-197 (1986).

U.S. Pat. Nos. 5,378,688; 5,488,036; and 5,492,893 disclose compounds said to be useful in inducing sterility in mammals, and in treating certain sex hormone-related cancers in mammals. The disclosed compounds were generically described as GnRH (or a GnRH analog) conjugated to a toxin. The toxin was preferably linked to the sixth amino acid of the GnRH agonist. The toxin was preferably one with a translocation domain to facilitate uptake into a cell. The inventors noted that conjugation of the GnRH agonist to the toxin "is necessary because, for the most part, the above toxins, by themselves, are not capable of binding with cell membranes in general. That is to say that applicants have found that it is only when a GnRH analog of the type described herein is linked to a toxin of the type noted above does that toxin become capable of binding to cell membranes . . . ." (E.g., U.S. Pat. No. 5,488,036, col. 7, lines 46-52.) The toxins specifically mentioned appear all to have been metabolic toxins, for example ricin, abrin, modeccin, various plant-derived ribosome-inhibiting proteins, pokeweed antiviral protein, α-amanitin, diphtheria toxin, pseudomonas exotoxin, shiga toxin, melphalan, methotrexate, nitrogen mustard, doxorubicin, and daunomycin. None of these toxins is believed to be toxic due to direct interaction with the cell membrane. In the in vivo experiments reported, the most effective time course was reported to be weekly injections for 4 weeks. (E.g., U.S. Pat. No. 5,488,036, col. 20, lines 46-47.) Because most of the conjugates cited are relatively large compounds, antigenicity could be a problem when such multiple administrations are used. The GnRH analog was preferably linked to the toxin with one of several specified heterobifunctional reagents. The specifications suggest that considerable effort was expended in conjugating the toxin to the GnRH agonist. The toxins must in general be internalized into the target cells to have effect, and do not act on cell membranes; in addition, at least some of these toxins must be secondarily transported from the membrane-bound vesicle into the cytoplasm to interact with ribosomes, mitochondria, or other cellular components.

M. Kovacs et al., "Recovery of pituitary function after treatment with a targeted cytotoxic analog of luteinizing hormone-releasing hormone," *Proc. Natl. Acad. Sci. USA*, vol. 94, pp. 1420-1425 (1997) discloses that a doxorubin analog conjugated to an LH-RH (i.e., GnRH) agonist selectively attacked cells with LH-RH receptors, and that its effect on pituitary cells was reversible. The paper suggests that the conjugate might be used to treat tumors with LH-RH receptors. See also A. Jungwirth et al., "Regression of rat Dunning R-3227-H prostate carcinoma by treatment with targeted cytotoxic analog of luteinizing hormone-releasing hormone AN-207 containing 2-pyrrolinodoxorubicin," *Intl. J. Oncol.*, vol. 10, pp. 877-884 (1997)

R. Moretti et al., "Luteinizing hormone-releasing hormone agonists interfere with the stimulatory actions of epidermal growth factor in human prostatic cancer cell lines, LNCaP and DU 145," *J. Clin. Endocrin. & Metab.*, vol. 81, pp. 3930-3937 (1996) discloses that LH-releasing hormone agonists inhibit both androgen-dependent (LNCaP) and androgen-independent (DU 145) human prostatic cancer cell lines, and suggests that the agonists may inhibit proliferation of the tumor cells by interfering with the stimulatory actions of epidermal growth factor.

I. Mezô et al., "Synthesis of GnRH analogs having direct antitumor and low LH-releasing activity," *J. Med. Chem.*, vol. 40, pp. 3353-3358 (1997) discloses chicken I GnRH agonists and antagonists. Agonist MI-1892 was reported to have low endocrinological activity, but to possess antitumor activity.

A. Nechushtan et al., "Adenocarcinoma cells are targeted by the new GnRH-PE$_{66}$ chimeric toxin through specific gonadotropin-releasing hormone binding sites," *J. Biol. Chem.*, vol. 272, pp. 11597-11603 (1997) discloses the use of a *Pseudomonas* exotoxin coupled to GnRH to kill certain types of cancer cells.

X. Zhu, "Steroid-independent activation of androgen receptor in androgen-independent prostate cancer. A possible role for the MAP kinase signal transduction pathway?" *Mol. & Cell. Endocrinol.*, vol. 134, pp. 9-14 (1997) discloses that androgen receptors in prostate cancer could be activated in the absence of the androgen signal.

G. Emons et al., "Growth-inhibitory actions of analogues of luteinizing hormone releasing hormone on tumor cells," *Trends in Endocrin. Metab.*, vol. 8, pp. 355-362 (1997) reviews the similarities and differences between GnRH receptors of cancer cells and of normal brain and pituitary cells; and suggests that LHRH analogs interfere with the mitogenic signal transduction of growth-factor receptors and related oncogene products associated with tyrosine kinase activity in a number of malignant human tumors, including breast, ovary, endometrium, and prostate cancers.

D. Tang et al., "Target to Apoptosis: A Hopeful Weapon for Prostate Cancer," *The Prostate*, vol. 32, pp. 284-293 (1997) provides a review of research on apoptosis as a route to treat prostate cancers.

A. Goustin et al., "Growth Factors and Cancer," *Cancer Research*, vol. 46, pp. 1015-1029 (1986) provides an overview of various growth factors that have been associated with different cancers.

S. Cho et al., "Evidence for autocrine inhibition of gonadotropin-releasing hormone (GnRH) gene transcription by GnRH in hypothalamic GT1-1 neuronal cells," *Mol. Brain Res.*, vol. 50, pp. 51-58 (1997) discloses that neuroendocrine populations of GnRH neurons have high affinity receptors for GnRH and for GnRH analogs.

S. Sower et al., "Primary structure and biological activity of a third gonadotropin-releasing hormone from lamprey brain," *Endocrinology*, vol. 132, pp. 1125-1131 (1993) describes the structure of lamprey III GnRH.

E. Stopa et al., "Immunocytochemical evidence for a lamprey-like gonadotropin-releasing hormone in human brain," *Soc. Neurosci. Abstr.*, abstract no. 437.8, p. 1577 (1987) discloses that a lamprey-like GnRH III is found in humans.

S. White et al., "Three gonadotropin-releasing hormone genes in one organism suggest novel roles for an ancient peptide," *Proc. Natl. Acad. Sci. USA*, vol. 92, pp. 8363-8367 (1995); and J. Powell et al., "Three forms of gonadotropin-releasing hormone characterized from brains of one species," *Proc. Natl. Acad. Sci. USA*, vol. 91, pp. 12081-12085 (1994) are examples of papers reporting the typical presence of three forms of GnRH in species of vertebrates.

J. Warnock et al., "Anxiety and mood disorders associated with gonadotropin-releasing hormone agonist therapy," *Psychopharmacology Bull.*, vol. 33, pp. 311-316 (1997) reports that psychological side effects can accompany chronic treatment with a GnRH agonist.

L. Deligdisch et al., "Pathological changes in gonadotropin releasing hormone agonist analogue treated uterine leiomyomata," *Fertility and Sterility*, vol. 67, pp. 837-841 reported the pathological changes associated with treating leiomyomata with a GnRH analog to induce iatrogenic menopause.

J. Fuerst et al., "Effect of active immunization against luteinizing hormone-releasing hormone on the androgen-sensitive Dunning R3327-PAP and Androgen-Independent Dunning R3327-AT2.1 prostate cancer sublines," *Prostate*, vol. 32, pp. 77-84 (1997) reported that active immunization of rats with an LHRH-diphtheria toxoid conjugate caused atrophy of the testes, prostate, and androgen-sensitive prostate tumors, with inhibition of the tumors caused by suppression of cell division rather than an increase in cell death; and that the volume increase of androgen-independent prostate tumors was slightly reduced.

C. Mantzoros et al., "Insulin-like growth factor 1 in relation to prostate cancer and benign prostatic hyperplasia," *Br. J. Cancer*, vol. 76, pp. 1115-1118 (1997) reported that increased levels of insulin-like growth factor 1 were associated with an increased risk of prostate cancer.

V. Ding, "Sex hormone-binding globulin mediates prostate androgen receptor action via a novel signaling pathway," *Endocrinology*, vol. 139, pp. 213-218 (1998) reported that androgen-independent pathways may activate the progression of some prostate cancers.

J. King et al., "Evolution of gonadotropin-releasing hormones," *Trends in Endocrin. Metab.*, vol. 3, pp. 339-344 (1992) discloses the primary structures of different GnRHs from various vertebrates. See also J. King et al., "Structure of chicken hypothalamic luteinizing hormone-releasing hormone. II. Isolation and characterization," *J. Biol. Chem.*, vol. 257, pp. 10729-10732 (1982).

N. Mores et al., "Activation of LH receptors expressed in GnRH neurons stimulates cyclic AMP production and inhibits pulsatile neuropeptide release," *Endocrinology*, vol. 137, pp. 5731-5734 (1996) discloses that LH acts directly on neuroendocrine neurons in the brain. See also Z. Lei et al., "Signaling and transacting factors in the transcriptional inhibition of gonadotropin releasing hormone gene by human chorionic gonadotropin in immortalized hypothalamic GT1-7 neurons," *Mol. & Cell. Endocrinology*, vol. 109, pp. 151-157 (1995).

U.S. Pat. Nos. 5,597,945 and 5,597,946 disclose plants transformed with genes encoding various lytic peptides.

DISCLOSURE OF INVENTION

It has been unexpectedly discovered that amphipathic lytic peptides are ideally suited to use in a ligand/cytotoxin combination to specifically inhibit abnormal or normal cells that are driven by or are dependent upon a specific ligand interaction; for example, to induce sterility or long-term contraception, or to attack tumor cells, or to selectively lyse virally-infected cells, or to attack lymphocytes responsible for autoimmune diseases. The peptides act directly on cell membranes, and need not be internalized.

For example, administering a combination of gonadotropin-releasing hormone (GnRH) (or a GnRH agonist) and a membrane-active lytic peptide produces long-term contraception or sterilization in animals in vivo. Particularly surprising, sterility results even when the combination is administered to a sexually immature animal: The combination then prevents sexual maturation.

Administering in vivo a combination of a ligand and a membrane-active lytic peptide kills cells with a receptor for the ligand. The compounds used in the present invention are relatively small, and will not be antigenic. (Lytic peptides are known not to be very antigenic; and the ligands are not antigenic at all.) The compounds may be administered in a single dose, or in two or more closely spaced doses. Lysis of gonadotropes has been observed to be very rapid (on the order of ten minutes.) Lysis of tumor cells is rapid. The two components—the ligand and the lytic peptide—may optionally be administered as a fusion peptide, or they may be administered separately, with the ligand administered slightly before the lytic peptide, to activate cells with receptors for the ligand, and thereby make those cells susceptible to lysis by the lytic peptide. If a fusion peptide is used, it has been unexpectedly discovered that a linking moiety is not necessary to join the ligand to the lytic peptide: one may be bonded directly to the other, without the need for any intervening linkage; bonding may be performed by bonding one end of the ligand to one end of the peptide, or by bonding to the middle of either. The toxin, the lytic peptide, does not need a translocation domain, and need not be internalized, as it binds to and acts directly on the activated cell membrane to cause lysis. The ligand may be a full native compound, or it may instead be the binding domain alone; the latter is preferred where the full ligand is relatively large.

The compounds of the present invention are well-suited for use in gene therapy to treat malignant or non-malignant tumors, and other diseases caused by clones or populations of "normal" host cells bearing specific receptors (such as lymphocytes), because genes encoding a lytic peptide or encoding a lytic peptide/peptide hormone fusion may readily be inserted into hematopoietic stem cells or myeloid precursor cells.

MODES FOR CARRYING OUT THE INVENTION

Several cancer cells (uterine, endometrial, prostate, testicular, and ovarian) express LH or hCG receptors. Tao et al., "Expression of Luteinizing Hormone/Human Chorionic Gonadotropin Receptor Gene in Benign Prostatic Hyperplasia and in Prostatic Carcinoma in Humans," *Biol. Reprod.*, vol. 56, pp. 67-72 (1997). Conjugates of a lytic peptide and LH or a portion of the LH molecule may thus be used to destroy these cells selectively. For example, the genes encoding such hormones as FSH, TRH, and LH are known, and may be linked to a DNA sequence encoding a lytic peptide to produce a secreted fusion peptide, all under the control of a suitable promoter such as the acute-phase responsive promoters disclosed in U.S. patent application Ser. No. 08/474,678, filed Jun. 7, 1995, and in PCT application WO 95/01095, published Jan. 12, 1995. A binding site from a hormone may be used in lieu of the entire hormone, for example the fifteen amino acid binding site of LH and hCG. See D. Morbeck et al., "A Receptor Binding Site Identified in the Region 81-95 of the β-Subunit of Human Luteinizing Hormone (LH) and chorionic gonadotropin (hCG)," *Molecular and Cellular Endocrinology*, vol. 97, pp. 173-181 (1993).

A powerful vector that is suitable for transforming cells to be used in gene therapy is the transposon-based vector that is disclosed in U.S. Pat. No. 5,719,055.

It is known that the D-amino acid form of GnRH will bind to gonadotropes in the pituitary, to GnRH neurons in the brain, and to various types of cancer cells. It is also known that the D-amino acid forms of lytic peptides have essentially the same propensity to lyse cell membranes as do the L-amino acid forms. Compounds of the present invention (whether administered as a fusion peptide or separately) may therefore be administered either in L-form or D-form. D-form peptides, although generally more expensive than L-form, have the advantage that they are not degraded by normal enzymatic processes, so that the D-form peptides may therefore be administered orally and generally have a longer biological half-life. Oral administration of the D-form peptide may be enhanced by linking the peptide/hormone fusion product to a suitable carrier to facilitate uptake by the intestine, for example vitamin $B_{12}$, following generally the $B_{12}$-conjugation technique of G. Russell-Jones et al., "Synthesis of LHRH Antagonists Suitable for Oral Administration via the Vitamin $B_{12}$ Uptake System," *Bioconjugate Chem.*, vol. 6, pp. 34-42 (1995).

GnRH or GnRH analogs (collectively, "GnRH agonists") may be used in the present invention. It has been reported that substitutions at the 6 and 10 positions of the GnRH decapeptide can produce "superagonists" having greater binding affinity to the GnRH receptor than does GnRH itself. These "superagonists" include goserelin, leuprolide, buserelin, and nafarelin. See U.S. Pat. No. 5,488,036.

Without wishing to be bound by this theory, it is believed that a mechanism (though not the exclusive mechanism) underlying the sterilization/long term contraception aspect of this invention is as follows: GnRH activates gonadotropic cells in the pituitary gland, as well as neuroendocrine GnRH neurons in the brain. The activated cells have substantially increased susceptibility to lysis by a lytic peptide. The lytic peptide then preferentially destroys (or severely damages) these activated cells. When the gonadotrophic cells in the pituitary are destroyed and are deprived of GnRH from the brain, the pituitary no longer secretes follicle stimulating hormone (FSH) or luteinizing hormone (LH), rendering the animal temporarily or permanently sterile.

Although the ligand and the lytic peptide may be administered separately, it is preferred to link the two in a single molecule, because such a linkage greatly increases the effective concentration of the lytic peptide in the vicinity of ligand-activated cells. Furthermore, this increase in the effective lytic peptide concentration can obviate the need for activation of the cells, allowing the peptide to be linked to a binding site of a ligand alone, without needing to include the "remainder" of a native ligand that would normally be needed for activating the target cells. This linkage may be in either order: for example, GnRH/peptide or peptide/GnRH. Examples are modified GnRH/hecate (SEQ. ID NO. 3) and hecate/modified GnRH (SEQ. ID NO. 4). Note that no intermediate linker is necessary, and that the carboxy terminus of one of the two peptides may be bonded directly to the amino terminus of the other. (We have found that the initial pyro-glutamic acid residue of GnRH or of the GnRH portion of a fusion peptide may be substituted with glutamine without substantially changing the activity of the respective peptides. See, e.g., SEQ. ID Nos. 9, 3, and 4.)

Experimental Results

EXAMPLES 1-6

The pituitary gland of an adult female rat was harvested and divided into six sections of approximately equal size. One section was placed in each of six wells containing tissue culture medium at 37° C. A different treatment was applied to each well, as described below. Ten hours after treatment, the tissue from each well was fixed, and the histology of each was examined microscopically.

Treatment 1 applied tissue culture medium alone as a control. The histology of this tissue after treatment appeared normal.

Treatment 2 was an application of 5 nanograms of GnRH (SEQ. ID NO. 1) per mL of medium. The histology of this tissue after treatment was normal; a small degree of cellular vacuolization was noted. For comparison, the concentration of GnRH in normal, untreated rats varies from as low as 1 ng/mL to as high as 20 ng/mL during the LH surge phase of the estrous cycle.

Treatment 3 was an application of 50 μM of the lytic peptide hecate (SEQ. ID NO. 2) in the medium. The histology of this tissue after treatment appeared normal.

Treatment 4 was an initial application of 5 nanograms of GnRH per mL of medium for 15 minutes. Following this incubation, the medium containing GnRH was removed, and the tissue was washed once with plain medium. This medium was then removed, and was replaced with medium containing 50 μM of the lytic peptide hecate. Widespread basophilic (gonadotropic) cellular destruction was observed after this treatment.

Treatment 5 was an application of 50 μM of the fusion peptide modified GnRH/hecate (SEQ. ID NO. 3). Widespread basophilic (gonadotropic) cellular destruction was observed after the treatment.

Treatment 6 was an initial application of the fusion peptide GnRH/hecate (SEQ. ID NO. 3), followed by a second application of the fusion peptide GnRH/hecate two hours later. After treatment the tissue was virtually destroyed, with only stromal cells remaining.

EXAMPLE 7

Two sexually immature female rats from the same litter (age 33 days) were given two intravenous injections of saline control solution 24 hours apart. After the rats reached breeding age, they were examined 105 days post-inoculation. The external genitalia appeared normal. During a fourteen-day monitoring period 107 days to 121 days post-inoculation, each of the control rats completed at least two estrous cycles. The rats were then sacrificed and necropsied. The reproductive organs appeared histologically normal.

EXAMPLE 8

Two sexually immature female rats from the same litter as those of Example 7 (age 33 days) were given two intravenous injections of 500 μg GnRH/hecate fusion peptide in saline 24 hours apart. After the rats reached breeding age, they were examined 105 days post-inoculation. The external genitalia appeared small. Unlike the control rats, insertion of a cotton-tipped swab into the vagina was difficult. During a fourteen-day monitoring period 107 days to 121 days post-inoculation, neither of the treated rats demonstrated estrous or metestrous. The rats were then sacrificed and necropsied. The peptide-treated rats had thinned, inactive uterine and oviductal epithelia. Their ovaries contained no large follicles, and had a high number of atretic follicles (i.e., those that had failed to ovulate).

EXAMPLES 9-14

Eighteen sexually mature, mixed breed, female rats were randomly assigned to one of six groups containing three rats each. Each group of rats received a double treatment intravenously, as described below. Two weeks after the treatment, the rats were sacrificed and necropsied. The reproductive and endocrine organs were sectioned, weighed, and examined histologically.

Treatment 9 was a saline control. The rats in this group exhibited normal ovarian function (e.g., normal follicles and new corpora lutea). The pituitaries from this group were of normal size. Histology showed a normal number of pituitary basophilic cells.

Treatment 10 was injection with a total of 1.0 mg GnRH/hecate fusion peptide in saline, divided into two equal 0.5 mg injections administered 24 hours apart. The rats in this group showed an arrest of normal ovarian follicular development. Few corpora lutea were present, and those that were present appeared old. Follicles were large, and had not ruptured. Uterine morphology was consistent with hormonal inactivity. The pituitaries from this group were slightly smaller than the pituitaries from the saline control group. Histology revealed a 60% to 70% reduction in the number of pituitary basophilic cells compared to the controls.

Treatment 11 was injection of 100 μL of a 1.35 mM solution of GnRH (162 μg) in saline, followed 15 minutes later by injection with 100 μL of a 1.35 mM solution of hecate (337 μg) in saline. The same two-step treatment was repeated 24 hours later. The rats in this group showed altered ovarian histology. Few corpora lutea were present, and those that were present appeared old. Follicles were large, and had not ruptured. Uterine morphology was consistent with hormonal inactivity. The pituitaries and the pituitary histology were similar to those observed in Treatment 10.

Treatment 12 was injection of 100 μL of a 1.35 mM solution of hecate (337 μg) in saline. The treatment was repeated after 24 hours. The rats in this group exhibited normal ovarian function (e.g., normal follicles and new corpora lutea). The pituitaries and the pituitary histology were similar to those observed in Treatment 9.

Treatment 13 was injection of 100 μL of a 1.35 mM solution of GnRH (162 μg) in saline. The treatment was repeated after 24 hours. The rats in this group exhibited normal ovarian function (e.g., normal follicles and new corpora lutea). The pituitaries and the pituitary histology were similar to those observed in Treatment 9.

Treatment 14 was identical to Treatment 10, except that the GnRH/hecate fusion peptide was further purified by HPLC. The rats in this group showed an arrest of normal ovarian follicular development. Few corpora lutea were present, and those that were present appeared old. Follicles were large, and had not ruptured. Uterine morphology was consistent with hormonal inactivity. The pituitaries and the pituitary histology were similar to those observed in Treatment 10.

These experiments demonstrate that GnRH and the lytic peptide may be administered either separately or as a fusion peptide, although the fusion peptide is preferred as it is expected to be more active at lower doses.

Although experiments to determine optimum dosages had not been performed by the time this application is being filed, a person of ordinary skill in the art, who is given the teachings of the present specification, may readily ascertain optimum dosages through routine testing.

Although the experiments to date have been performed on female animals, similar results are expected for male animals, because GnRH signals pituitary cells to release gonadotropins in both males and females.

Tissue and cell specificity of cytotoxic conjugates could be further enhanced by using various hormones or hormone analogs coupled to a lytic peptide. Some examples follow. For fertility control, both the pituitary and the central GnRH neuronal component of the reproductive axis are selectively damaged by GnRH-hecate conjugate. Few cells in the central nervous system should be damaged by this treatment, because the chicken II GnRH and lamprey III GnRH forms are the primary molecules affecting brain function in most mammals. Fertility control may also be selectively accomplished by treating animals with a bLH-hecate conjugate; this compound should specifically affect GnRH neurons controlling reproduction and the gonads. To target prostatic, breast, ovarian, or endometrial cancer cells, the I-LHRH-III-hecate conjugate could be used since it binds to receptors on cancer cells, and has no significant known action on the brain. (Other lytic peptides may be used in place of hecate in these conjugates.)

The compositions of the present invention may be administered as described, or as pharmaceutically acceptable salts. The compositions may be administered intravenously, subcutaneously, intramuscularly, or orally (especially when in D-amino acid form, preferably complexed with a carrier, e.g., vitamin $B_{12}$).

Applications of the present invention include long-term contraception or sterilization in humans; and long-term contraception or sterilization in domesticated or wild mammals, birds, reptiles, amphibians, bony fish, cartilaginous fish, jawless fish, and invertebrates such as insects or molluscs. Domesticated mammals in which this invention may be used include, for example, dogs, cats, cattle, horses, pigs, and sheep. When used in humans, long-term replacement hormone therapy may be needed to prevent undesirable side effects, such as premature menopause. Administration of gonadotropic hormones in a sterilized individual will temporarily restore fertility if desired. The sterilization is reversible in this sense.

As one example, this invention may be used in the humane population control of an unwanted introduced species.

Sterilization of domesticated birds such as chickens and turkeys can increase their growth rate. Avian GnRH or analogs may be used in practicing this invention to sterilize birds. There are two forms of avian GnRH—Chicken I GnRH (SEQ. ID NO. 17) and Chicken II GnRH (SEQ. ID NO. 18). Either form of avian GnRH may be used in this invention. In a preferred embodiment, position 6 of Chicken I GnRH is linked to a lytic peptide such as hecate to form a fusion peptide. Alternatively, a GnRH agonist or antagonist may be used. A series of agonists and antagonists has been synthesized by I. Mezo et al., "Synthesis of GnRH analogs having direct antitumor and low LH-releasing activity," *Biomed. Peptides, Proteins & Nucleic Acids*, vol. 2, pp. 33-40 (1996).

When used to treat insects that are pests to crop plants or other plants, it may be desirable to incorporate genes encoding the peptide/ligand combination into the plant's genome, under the control of a promoter that expresses the peptide in tissues of the plant that are attacked by the insect, but not in tissues that are used for food. For example, in a potato a promoter could be used that is active in the leaves of the plant, but not in the tuber. Expression in the plant tissue could be constitutive, or alternatively could be induced by stimuli that induce the plant's native defense mechanisms, for example by placing the peptide gene under the control of native promoters that are so induced in plants. See, e.g., U.S. patent application Ser. No. 08/279,472, filed Jul. 22, 1994.

When used to sterilize aquatic animals such as fish or molluscs, the compounds of the present invention may be simply administered in the water, from which they will be taken up by the animals in adult, juvenile, or larval stages. Preferably, the peptides are encapsulated in liposomes, which are fed to the animals as spat, fry, juveniles, or adults; the animals feed on the liposomes, which then release the compounds into the animal's circulation, causing sterilization. Alternatively, the peptides may be injected into an animal that has reached sufficient size.

For example, the compounds may be used to sterilize undesirable exotic molluscs such as the zebra mussel. Sterilization of aquaculture species may also be desirable. For example, sterilization of oysters will prevent the oysters from ripening gonads in the summer (when they would otherwise do so), thereby improving their marketability.

EXAMPLES 15-22

Eight sexually mature, Sprague-Dawley female rats were randomly assigned to one of eight treatments. Each group of rats received a single treatment intravenously, as described below. Rats were sacrificed and necropsied either 48 or 96 hours after treatment. The ovaries, uterus, pancreas, liver, spleen, lungs, heart, thyroid, and adrenal glands were fixed in 10% buffered formalin; sectioned; and stained with H&E (hematoxylin and eosin) stain; except that the pituitary glands were stained with PAS (periodic acid-Schiff) stain with no counter-stain. The treatments were selected so that each animal received an equimolar amount of the compound with which it was treated.

Treatments 15 and 16 were IV-injection with 674 µg of D-hecate in 200 µL saline (1.35 mM). The rat in treatment 15 was sacrificed 48 hours after injection, and the rat in treatment 16 was sacrificed 96 hours after injection. No gross lesions were noted in the organs of either animal. The pituitary glands of both rats contained a normal number of PAS-positive cells.

Treatments 17 and 18 were IV-injection with 334 µg of GnRH in 200 µL saline (1.35 mM). The rat in treatment 17 was sacrificed 48 hours after injection, and the rat in treatment 18 was sacrificed 96 hours after injection. No gross lesions were noted in the organs of either animal. The pituitary glands of both rats contained a normal number of PAS-positive cells.

Treatments 19-22 were IV-injection with 1 mg GnRH-hecate fusion peptide (SEQ. ID NO. 3) in 100 µL saline (2.7 mM). The rats in treatments 19 and 20 were sacrificed 48 hours after injection, and the rats in treatments 21 and 22 were sacrificed 96 hours after injection. No gross lesions were noted in the organs of any of the four animals, other than the pituitary. The pituitary glands of the animals from treatments 19 and 20 were slightly enlarged, hyperemic, and edematous. The pituitary glands of the animals from treatments 21 and 22 were slightly hyperemic, but of expected size. The pituitary glands of all four rats showed a marked depletion of PAS-positive cells; it was estimated that the depletion was 80 to 90% compared to those of control groups. (PAS stain preferentially stains glycopeptides. LH, FSH, TSH, and MSH are glycopeptide hormones; cells containing these hormones stored in their secretory vacuoles stain positive with PAS.)

It was thus seen that the GnRH-lytic peptide combination caused morphological and functional alterations in the adult female rat reproductive system, and in preventing sexual maturity in pre-pubertal female rats, but that the fusion peptide selectively eliminated a specific population of PAS-positive staining cells in the pituitary.

EXAMPLE 23

Hecate is an amphipathic lytic peptide that acts on cell membranes without being internalized. It is a synthetic peptide analog of melittin, the primary toxin in honeybee venom. Hecate is believed to act by disrupting cell membranes. The structure of the modified GnRH-hecate conjugate used in these studies was SEQ. ID NO. 3.

We also synthesized D-Lys⁶GnRH (SEQ. ID NO. 13), so that hecate could be conjugated to the D-Lys⁶, a position that could minimize interference with binding of the GnRH domain to the GnRH receptor. These synthetic peptides specifically displaced radiolabelled monoiodinated-GnRH from rat pituitary membranes. Displacement by D-Lys⁶GnRH-hecate was comparable to (and actually slightly greater than) displacement by native mammalian GnRH, as measured by cpm of radioactivity. When GnRH and GnRH-hecate binding were compared on a molar basis over a 1000-fold concentration range (n=6) the GnRH-hecate specifically displaced the radiolabelled peptide to an extent equal to 123%±4% of the binding exhibited by equimolar concentrations of GnRH; equimolar concentrations of D-Lys⁶GnRH displaced 187%±8% of the cpm displaced by native GnRH.

EXAMPLES 24-31

We studied in vitro lysis of bovine luteal cells with GnRH-hecate conjugate and with hecate-bLH conjugate (SEQ. ID NO. 12). (The bLH component of the conjugate is a 15-mer fragment of the beta chain of luteinizing hormone, SEQ. ID NO. 11). Small luteal cells were collected from cattle corpora lutea post-slaughter. Small luteal cells are rich in LH receptors, and were found to be highly susceptible to lysis by the hecate-bLH conjugate.

Small luteal cells in culture were incubated with one of the following treatments for 22 hours, and were then examined for viability using Trypan Blue exclusion and release of lactic dehydrogenase.

Treatment 24 control: no additional treatment (media alone)
Treatment 25 10 ng bLH (positive control)
Treatment 26 hecate-bLH, 10 μM
Treatment 27 hecate-bLH, 5 μM
Treatment 28 hecate-bLH, 1 μM
Treatment 29 hecate (alone), 10 μM
Treatment 30 hecate (alone), 5 μM
Treatment 31 hecate (alone), 1 μM Significant killing of small luteal cells was observed following 22 hr. incubation with 10 μM hecate alone, and with 5 μM hecate alone (approximately 50% killing). Cell death for 1 μM hecate alone did not differ significantly from negative control (media) or from bLH alone. All three treatment doses with hecate-bLH caused significant increases in cell death as compared to treatment with hecate alone. The hecate-bLH conjugate killed approximately twice the number of cells as were killed by hecate alone at the same concentrations.

Observed levels of lactic dehydrogenase activity also demonstrated that the hecate-bLH treatment killed a significantly greater number of cells than did hecate alone.

EXAMPLES 32-33

We also studied in vitro lysis of bovine granulosa cells with GnRH-hecate conjugate and with hecate-bLH conjugate. Granulosa cells were isolated from bovine pre-ovulatory follicles. (Granulosa cells are hormonally active cells with numerous LH receptors.) Our experiments with granulosa cells were otherwise generally similar to those described above for Examples 24-31. These experiments demonstrated (1) that the granulosa cells were much more susceptible to killing by hecate alone than were the small luteal cells, and (2) that, as had been the case with the small luteal cells, the granulosa cells were significantly more susceptible to hecate-bLH at even the lowest concentration (1 μM) than they were to hecate alone. At 1 μM, the hecate-bLH conjugate killed about twice the number of target cells as did hecate alone. Again, the levels of lactic dehydrogenase released following the hecate-bLH 1 μM treatment were significantly higher than the levels of enzyme released following treatment with 1 μM hecate alone.

Additional studies (data not shown) demonstrated that a 15-mer fragment of the bLH subunit specifically bound to LH receptors on the target granulosa cells, but did not initiate the production of steroid hormones that would be indicative of a stimulus-coupled response. We thus demonstrated that the selective killing of target cells resulted from the physical proximity of the lytic peptide to the cell, which was caused by binding of the LH subunit. Stimulation of target cell hormone production was not required for cell lysis. This result was surprising, as we had previously expected that activation of the target cells was required for increased susceptibility to lysis. These data demonstrate that such activation is not required. These data are, however, consistent with our other data showing that cell activation is also a route that can lead to increased susceptibility to the lytic peptide.

EXAMPLES 34-37

Another set of experiments was performed to study the in vivo effects of the GnRH-hecate conjugate on female rats and rabbits. The ovaries, uterus, oviducts, adrenals, spleen, thyroids, pancreas, liver, lungs, and heart were processed for histological analysis. The pituitaries were processed for histological analysis of PAS-stained cells and for cells stained immunocytochemically for bLH, BFSH (bovine follicle stimulating hormone), adrenocorticotropic hormone, and other proopiomelanocortin peptide products (most notably alpha-melanocyte stimulating hormone (MSH)), thyroid stimulating hormone (TSH), prolactin (PRL), vasopressin (VP), oxytocin (OXY) or growth hormone (GH). The immunocytochemical staining procedures we used followed generally the procedures of M. Rahmanian et al., "Histological and immunocytochemical characterization of pituitary cell types in ponies," Proc. 13th Soc. Equine Nutrition & Phys. Symp., pp. 348-349 (1993); M. Rahmanian et al., "Immunocytochemical localization of luteinizing hormone and follicle-stimulating hormone in the equine pituitary," J. Anim. Sci., vol. 76, pp. 839-846 (1998); M. Rahmanian et al., "Immunocytochemical localization of prolactin and growth hormone in the equine pituitary," Animal Sci., vol. 75, pp. 3010-3018 (1997); and P. Melrose et al., "Comparative topography of the immunoreactive alpha-melanocyte-stimulating hormone neuronal system in the brains of horses and rats," Brain Beh. & Evol., vol. 32, pp. 226-235 (1988).

Brains were serially sectioned on a Vibrotome from the level of the diagonal band of Broca to the mammillary body. Alternate sections were consecutively divided into four to five dishes, and sections in alternate dishes were stained with cresyl violet, or were stained immunocytochemically for GnRH or the GnRH precursor, VP, OXY, or tyrosine hydroxylase (the rate-limiting enzyme in catecholamine synthesis). In addition to the staining procedures cited above, we also used the immunocytochemical staining procedures of P. Melrose et al., "Distribution and morphology of immunoreactive gonadotropin-releasing hormone (GnRH) neurons in the basal forebrain of ponies," J. Comp. Neurol. vol. 339, pp. 269-287 (1994); and P. Melrose et al., "Topography of oxytocin and vasopressin neurons in the forebrain of Equus caballus: Further support of proposed evolutionary relationships for proopiomelanocortin, oxytocin and vasopressin neurons," *Brain, Beh. & Evol.*, vol. 33, pp. 193-204 (1989).

Thirty-three-day-old, sexually immature female rats were given intravenous administrations as follow:

Treatment 34: 0.03 μg GnRH (a normal physiological dose) (two rats)

Treatment 35: 1.62 μg GnRH (the molar equivalent to the amount of GnRH in Treatment 36) (one rat)

Treatment 36: 0.5 mg GnRH-hecate (one rat)

Treatment 37: 0.03 μg GnRH, followed 11 minutes later by 0.337 μg hecate (two rats).

Animals were sacrificed 14 days after treatment. As compared to the two GnRH control groups, the treatment with GnRH-hecate and the treatment with GnRH followed by hecate alone reduced pituitary weights by 13% and 14%, respectively, and reduced the numbers of bLH-specific gonadotropes by 92% and 87%, respectively. Further, following these two experimental treatments the cell bodies of GnRH-stained neurons in hypophysiotropic areas of the brain were frequently deformed; and a substantial amount of immunoreactive material leached into surrounding areas where numerous cell bodies are concentrated (the organum vasculosum of the lamina terminalis). There was histological damage to cells from the two experimental treatments in the C1 and C3 fields of the hippocampus, and increased staining of parvicellular VP neurons in the paraventricular nucleus. (The VP staining may have been caused by formation of a precipitate in certain areas of the brain. Subsequent studies with more highly purified peptide did not show a precipitate). The change in VP expression, probably in corticotropin-releasing neurons, may cause a shift in the post-translational processing of proopiomelanocortin peptide products in the pars distalis, since GnRH-hecate and GnRH+hecate treatments reduced adrenocorticotropic hormone levels and increased the number of alpha-MSH-stained cells in this subdivision of the pituitary. No pathological changes were noted in any other tissues.

Since neurons in the brain do not regenerate, severe damage to these neurons could make sterilization with a GnRH/lytic peptide combination permanent (but temporarily reversible by administration of gonadotrophic hormones).

EXAMPLES 38-42

Sexually immature (33 day old) female rats (randomly allocated into groups of three) were injected intravenously with saline or GnRH-hecate in saline as follows:

Treatment 38: 0.0 mg GnRH-hecate
Treatment 39: 0.1 mg GnRH-hecate
Treatment 40: 0.5 mg GnRH-hecate
Treatment 41: 1.0 mg GnRH-hecate
Treatment 42: 1.5 mg GnRH-hecate.

Animals were sacrificed at 24 hours or at 14 days after treatment. Results were similar to those reported above for Examples 34-37, except that no precipitate was found in the brain, and VP staining in the CNS was not altered. The treatments with higher levels of GnRH-hecate produced a large number of GnRH-receptor-containing neurons having abnormal morphologies, including distortion of the somatic portion of the cells, and degeneration of neurites. In the rats sacrificed fourteen days after treatment, 66% and 87% of the GnRH-receptor-containing neurons were abnormal in the rats that had received 1.0 and 1.5 mg of GnRH-hecate, respectively. Axonal degeneration in the 1.5 mg GnRH-hecate group was accompanied by over 90% reduction in median eminence staining for GnRH.

EXAMPLES 43-45

Seven sexually mature female New Zealand rabbits were injected intravenously with saline containing GnRH-hecate as follows:

Treatment 43: 0 mg GnRH-hecate (n=3)
Treatment 44: 5 mg GnRH-hecate (n=3)
Treatment 45: 10 mg GnRH-hecate (n=1).

Forty-six days later all rabbits were injected intramuscularly with 100 μg GnRH. Blood samples were collected at 0, 1, 4, and 24 hours, and LH and FSH levels in the blood samples were measured by radioimmunoassay. Hormone analyses revealed that both control and experimental animals released LH in response to the GnRH, suggesting that there may be at least some degree of reversibility following treatment, at least for pituitary gonadotropes at lower doses of ligand/peptide. The rabbits were sacrificed the next day (day 47) for postmortem histological analysis. We found that the numbers of tertiary follicles, corpora lutea, and GnRH-induced ovulations were reduced by GnRH-hecate treatment. Ovarian and pituitary weights were reduced by the 10 mg GnRH-hecate treatment. In tissues from the GnRH-hecate treatments, observed immunoreactive GnRH was faint and diffusely localized in CNS areas normally containing cell bodies; normal individual cell bodies were reduced in number by at least 50%; and the terminal fields, which normally contain the axons of GnRH receptor neurons, were not stained for GnRH. These observations suggest that the most pronounced effects of the GnRH-hecate treatments in these experiments on rabbits may have been on neuroendocrine neurons in the brain. The hippocampus and other areas of the brain containing high concentrations of GnRH were not discernibly affected by GnRH-hecate treatments. The GnRH-hecate treatment increased the number of PAS-stained pituitary cells in the pars distalis to 177% of that for control rabbits; this increase appeared to reflect increased numbers of cells staining alpha-MSH, and reduced numbers of cells staining for LH.

EXAMPLES 46-47

Nine sexually mature female rabbits were injected intravenously with saline containing 0 mg (n=4) (Treatment 46) or 10 mg GnRH-hecate (n=5) (Treatment 47). Rabbits were injected intramuscularly with GnRH on day 6 posttreatment. Blood samples were collected for radioimmunoassay of LH and FSH as described above, and the animals were sacrificed on day 7 post-treatment. Both control and experimental animals released LH in response to the GnRH; however, the amount of LH released was lower in the treated animals than in the controls. The GnRH-hecate treatment reduced the numbers of tertiary ovarian follicles, and the numbers of GnRH-induced ovulations. No effects were noticed either on peripheral tissues or on pituitary weight. The effects of GnRH-hecate on CNS morphology and immunocytochemical results were similar to those described above in Examples 34-45. Again, the effects were more pronounced on GnRH neurons than on staining of pituitary gonadotropes.

The number of ovulation sites in rabbits in Examples 46 and 47 treated with 10 mg GnRH-hecate were reduced as compared to saline controls. The mean number of ovulation sites in four saline controls equalled 12.2±5.4, with S.E.M.=2.7. The mean number of ovulation sites in the five rabbits given 10 mg of GnRH-hecate was 3.6±1.1, with S.E.M.=0.5. This difference from control was significant (p=0.025).

The "LH surge" (the level of LH at one hour post-GnRH challenge, minus the resting level before challenge) in the four controls was 61.2±16.5 ng/mL, with S.E.M.=8.3; and in the treated group was 49.6±26.1 ng/mL, with S.E.M.=12 (p=0.22). Thus there was a trend towards lower LH levels in the treated group.

The in vivo studies clearly demonstrated that the GnRH-hecate conjugate selectively damaged GnRH receptor-bearing cells in the brain (neurons) and in the pituitary (gonadotrophic cells). Further, these studies demonstrated a significant alteration in the ovary, presumably a consequence of alteration in the reproductive centers of the brain-pituitary axis. Selectivity of the conjugate was demonstrated by the following observations: (1) No cytotoxic changes were seen in neurons that lacked GnRH receptors. (2) No changes were seen in pituitary cells that lacked GnRH receptors. (3) No changes were seen in other endocrine and non-endocrine tissues (except for the ovary, which presumably responded indirectly to the destruction of gonadotrophs in the pituitary).

Many of the events referred to as "ovulations" in the GnRH-hecate treated rabbits possibly were not functional ovulation sites, but may instead have represented hemorrhagic pre-ovulatory degenerative changes. Additional breeding trials will be conducted to verify that ovulation of functional ova is prevented.

EXAMPLES 48-51

The following examples demonstrated the ability of a GnRH-lytic peptide combination to reduce fertility in insects. It was also unexpectedly discovered that the lytic peptide alone (i.e., administered without GnRH) had similar effects. Although insects are not believed to secrete a GnRH identical to that found in mammals, there appears to be some homology, in that the insects did respond to mammalian GnRH, and to GnRH linked to the lytic peptide hecate.

Late-stage *Diatraea saccharalis* (sugar cane borer) pupae were inoculated with 1.0 µL of saline solution containing 1.35 mM concentration of peptide as stated, or saline alone as control. The pupae were allowed to complete metamorphosis. No gross morphological defects were observed in any of the insects completing metamorphosis. Adult female moths were allowed to mate with treated males, and then lay eggs. The viability of the eggs was measured by counting the number hatching into larvae.

Treatment 48 was the control, inoculation of 21 pupae with saline alone. Twelve of the pupae completed metamorphosis into adult moths (4 males, 8 females). The 8 females laid a total of about 900 eggs, an average of about 112 eggs per female. About 22% of these eggs hatched, or about 25 hatched larvae per female.

Treatment 49 was inoculation of 10 pupae with 1.35 mM GnRH. Four of the pupae completed metamorphosis into adult moths (2 males, 2 females). The 2 females laid a total of about 300 eggs, or an average of about 150 eggs per female. About 40% of these eggs hatched, or about 60 hatched larvae per female.

Treatment 50 was inoculation of 10 pupae with 1.35 mM GnRH-hecate (SEQ. ID NO. 3). Eight of the pupae completed metamorphosis into adult moths (3 males, 5 females). The 5 females laid a total of about 200 eggs, or an average of about 40 eggs per female. About 40% of these eggs hatched, or about 16 hatched larvae per female.

Treatment 51 was inoculation of 10 pupae with D-hecate. Six of the pupae completed metamorphosis into adult moths (2 males, 4 females). The 4 females laid a total of 18 eggs, or an average of 4.5 eggs per female. 100% of these eggs hatched, or 4.5 hatched larvae per female.

It was thus observed that, compared to controls, females treated with GnRH alone in the late pupal stage had enhanced reproductive success; those treated with the GnRH-hecate combination had decreased reproductive success; and those treated with D-hecate alone had even lower reproductive success.

Without wishing to be bound by the following hypothesis, it is believed that these results may be explained as follows. Due to (as yet unidentified) sequence homology across taxa, small peptides active in the control of mammalian reproduction also influence reproductive function in insects. See W. Theunis et al., "Luteinising Hormone, Follicle Stimulating Hormone and Gonadotropin Releasing Hormone Immunoreactivity in Two Insects: *Locusta migratoria* migratoroides R & F and *Sarcophaga bullata* (Parker)," *Invert. Reprod. and Develop.*, vol. 16, pp. 111-117 (1989); and P. Verhaert et al., "Substances Resembling Peptides of the Vertebrate Gonadotropin System Occur in the Central Nervous System of *Periplaneta americana* L.," *Insect Biochem.*, vol. 16, pp. 191-197 (1986).

This activity is probably mediated by the inherent ability of these peptides to react with appropriate intermediate cells by a ligand-receptor interaction, thus altering the functional activity of the intermediate cells. More particularly, insects have a receptor that responds to mammalian GnRH. GnRH alone stimulates reproductive activity in insects. GnRH coupled to a lytic peptide attacks the intermediate cells in the insects, inhibiting reproductive activity.

The results observed for the D-hecate administered without GnRH were surprising, and are explained somewhat differently, again without wishing to be bound by the following hypothesis. Metamorphosis is a time of high cell activity. Lytic peptides generally have greater activity against active cells. The observed response to hecate alone is believed to be a generalized response by activated cells, not a specific response mediated by a receptor. The fact that the D-conformation of hecate was used in this experiment may be significant, since D-form peptides generally have a longer biological half-life. It is currently unknown whether similar results would be seen with L-hecate alone. (D-hecate was used in Treatment 26 for the simple reason that previously-synthesized D-hecate was readily available to the investigators.)

Treatment of Malignant and Benign Tumors

The compositions of the present invention are useful in killing or inhibiting the growth of malignant and benign tumor cells that express receptors for GnRH, LH, hCG, I-LHRH-III, or steroids. The ligand is administered with a lytic peptide (either sequentially, or linked to one another), and the targeted tumor cells are killed or inhibited.

In treating hormone- or ligand-linked cancers (e.g., cancers of the ovary, testis, breast, uterus, endometrium, pituitary, and prostate), lytic peptides may be attached to the hormone for which the tumor expresses a receptor or set of receptors, e.g., an estrogen, testosterone, LH, FSH, estradiol-17β, transforming growth factor alpha (TGFα), epidermal growth factor (EGF), GnRH, LH, hCG, lamprey III LHRH (I-LHRH-III), and melanocyte stimulating hormone. For example, an ester linkage of a lytic peptide to estradiol or testosterone can conveniently be made by condensing the carboxy terminus of the lytic peptide with the hydroxyl group at the 17-carbon position of the steroid. An estradiol/lytic peptide combination may be used as a treatment against breast or ovarian cancer; and a testosterone/lytic peptide combination may be used to treat prostate cancer. In addition, the specific binding domains of the peptide hormone LH or FSH may be used in fusion peptides with a lytic peptide to selectively bind the fusion peptide to target tumor cells with cell surface receptors for these hormones. For example, the receptor binding site of the β-subunit of LH and hCG may be used (SEQ. ID NO. 11). See Morbeck et al., *Mol. and Cell Endocrin.*, vol. 97, pp. 173-186 (1993).

Pituitary Tumors

The anterior pituitary contains different types of epithelial cells that control the complex processes of growth, reproduction, lactation, thyroid function, and adrenal functions. Due to the high functional plasticity of pituitary cells (i.e., their ability to differentiate into different cellular phenotypes in response to stimuli), these cells are particularly prone to aberrant behavior. Because many of the signals to which the pituitary responds are receptor-mediated, pathological states may be controlled by co-opting the appropriate ligand-receptor interaction. Several examples are given below.

Dopamine Receptors in Prolactinomas and Other Adenomas

Chronic dopamine deficiency has been associated with some types of pituitary tumors. In certain adenomas the number of dopamine binding sites is reduced by about 50%, and the number can be reduced even further during dopaminergic therapy. It has also been reported that nerve growth factor can stimulate prolactinoma cells to re-express dopamine receptors. Pretreating a prolactinoma with nerve growth factor before treatment with a dopamine/lytic peptide combination makes it susceptible to treatment through the present invention. The lytic peptide may be linked to dopamine, for examine, by an amide group formed by condensing the carboxy terminus of the peptide with the amino group of dopamine.

This therapy will be effective not only for prolactinomas, but also for other adenomas expressing dopamine receptors, such as growth hormone-secreting adenomas, thyrotropin-releasing hormone secreting adenomas, and gonadotropin-secreting adenomas.

Somatostatin Receptors in Growth Hormone-Secreting Adenomas

It has been reported that growth hormone (GH)-secreting adenomas have a highly variable number of somatostatin receptors. (Variation by at least a factor of 10 may be seen among individual tumors.) There is also considerable variation in the distribution of binding sites: the somatostatin receptors may be homogeneously distributed, located exclusively in one portion of the tumor tissue, or in between.

Somatostatin receptors are also present in other types of pituitary tumors. It has been reported that the cell surfaces of a majority of GH- and thyrotropin releasing hormone (TRH)-secreting adenomas have an elevated number of somatostatin receptors.

Such tumors may be treated by the present invention by a somatostatin/lytic peptide combination.

Other Pituitary Adenomas

Other ligands that may be used in a ligand/lytic peptide combination to treat other pituitary adenomas include TRH, MSH, GnRH, corticotropin-releasing hormone, growth hormone-releasing hormone, vasoactive intestinal polypeptide, and pituitary adenylate cyclase activating peptide. A short chain analog of αMSH that may be used in place of MSH is Ser-Tyr-Cys-Met-Glu-His-Phe-Arg-Trp-Asn-Lys-Pro-Val-NH$_2$ (SEQ. ID NO. 10).

Other Endocrine-Related Diseases

In other applications, the ligand/lytic peptide combination of the present invention may be used to treat endocrine-related diseases generally. Where a disease is causally related to dysfunction of cells having certain hormone receptors, cells with such receptors may be selectively inactivated by administering a combination of the hormone and a lytic peptide.

In an alternative approach, it has previously been noted that it is beneficial to reduce levels of LH and FSH in breast and prostate cancer patients. If the gonadotropes in the pituitary are selectively killed with a GnRH/lytic peptide combination, then the pituitary will no longer secrete LH and FSH. The reduced levels of these hormones thus resulting will help control the spread of the cancers. This alternative, indirect approach may be used in lieu of, or in addition to, treating the cancers directly with a LH/lytic peptide or FSH/lytic peptide combination. Chronic administration of GnRH has previously been used to down-regulate its receptors, and thus effectively remove LH from circulation, resulting in "chemical castration" of prostatic cancer patients. However, GnRH and certain GnRH analogs also have direct effects on prostatic cell growth.

By analogy, it is well-established that surgical removal of the anterior pituitary is effective in treating sex hormone-related diseases. Chemical destruction of gonadotrophic cells in the pituitary through the present invention will therefore have similar effects on sex hormone-related diseases, but without the attendant risks and complications of surgery.

EXAMPLES 52-58

In these experiments we demonstrated in vitro lysis of human prostate cancer cell lines. LNCaP FGC and DU145 human prostate cancer cell lines were purchased from the American Type Culture Collection (ATCC, Rockville Md.), ATCC accession numbers CRL 1740 and HTB-81, respectively. The LNCaP FGC adenocarcinoma cell line was originally obtained from a 50 year old male Caucasian. LNCaP FGC cells are sensitive to dihydrotestosterone and to estrogens (A+). The DU145 carcinoma was originally isolated from the brain of a 69 year old male Caucasian with metastatic carcinoma of the prostate; this cell line is not sensitive to steroid hormones (A−).

Cells were detached from culture flasks, and 1000 cells/well were transferred to 24 well culture plates. The cells were incubated for 24 hours with 10% calf serum. Cells were subsequently incubated without serum for 48 hours. Cells were then incubated for 22 hours with one of the following treatments:

Treatment 52: 10 µM luteinizing hormone (LH)
Treatment 53: 30 µM free hecate
Treatment 54: 90 µM hecate-bLH
Treatment 55: 60 µM hecate-bLH
Treatment 56: 50 µM GnRH-hecate
Treatment 57: 10 µM GnRH-hecate
Treatment 58: FSH pre-treatment, followed by 90 µM hecate-bLH Trypan blue exclusion was used to assess viability of the cells after treatment. The treatment that most consistently and effectively killed both the A+ and the A− cancer cell lines was the higher dose (50 µM) of GnRH-hecate. The lower dose (10 µM) of GnRH-hecate was equally effective against the androgen-insensitive DU145 cells. The DU145 cells were also killed by hecate alone. However, treatment with a lytic peptide alone may not be selective in vivo unless specific cell types are separately stimulated, for example by hormones controlling their activity. The hecate-bLH conjugate killed almost all DU145 cells, but had little effect on A+ LNCaP. This result is consistent with specific binding of LH to DU145 cells but not to LNCaP cells. LH specifically binds DU145 cells, but we have not been able to consistently measure specific binding of LH to the A+ LNCaP cells. The LNCaP cells pre-treated with FSH were more sensitive to the hecate-bLH conjugate than those that were not pre-treated.

Other Applications, including Treatment of Autoimmune Diseases, and Targeting of Abnormal Cells This invention may be used wherever it is desirable to specifically inhibit abnormal (or normal) cells that are driven by or are dependent on specific ligand interactions. As another example, this invention may be used in treating autoimmune diseases for which the antigen or epitope responsible for the autoimmune disease is known.

Specific immune responses are mediated by B-lymphocytes, T-lymphocytes, or both. When lymphocytes inappropriately attack "self" instead of "non-self," a variety of autoimmune diseases can result, some of which can have devastating consequences. Diseases that have been associated with autoimmunity include rheumatoid arthritis, juvenile rheumatoid arthritis, systemic lupus erythematosus, Addison's disease, Goodpasture's syndrome, autoimmune hemolytic anemia, Grave's disease, Hashimoto's thyroiditis, idiopathic thrombocytopenia purpura, insulin-dependent diabetes mellitus, myasthenia gravis, myocardial infarction, aplastic anemia, pernicious anemia, poststreptococcal glomerulonephritis, spontaneous infertility, ankylosing spondylitis, scleroderma, and Sjögrens' syndrome.

Whether mediated by T-cells or B-cells, autoimmune disease is characterized by lymphocytes with specific receptors for a self epitope that triggers their function—i.e., antibody secretion, proliferation, secretion of cytotoxic factors, or secretion of inflammatory cytokines. These responses cause damage or destruction to self cells or organs.

The specific antigens and even epitopes that act as ligands to stimulate the lymphocytes have been identified for several autoimmune diseases, typically by the in vitro proliferative response they induce in lymphocytes. For example, thyrotropin has been implicated as the self-antigen recognized by lymphocytes in Hashimoto's Disease. Where the epitope is known, the autoimmune disease may be treated by administering a compound containing that epitope linked to a lytic peptide, which will selectively delete clones of the autoreactive lymphocytes.

There have previously been no general treatments for autoimmune diseases. Prior treatments have included cytotoxic compounds, and high doses of corticosteroids, both of which have risks in long-term therapy. Neither selectively targets autoreactive lymphocytes.

Certain abnormal cells (e.g., virally-infected cells such as HIV-infected cells, cancer cells) display surface receptors that are not found on normal cells. In some cases, these receptors are encoded by viral nucleic acids. Ligands for these receptors, such as monoclonal antibodies to those receptors, or the receptor/ligand pairs shown in Table 2 of D. Fitzgerald et al., "Targeted Toxin Therapy for the Treatment of Cancer," *J. Natl. Cancer Inst.*, vol. 81, pp. 1455-1463, may be used in the ligand/lytic peptide combination of the present invention to selectively destroy cells displaying the receptor. Destruction of such a virally-infected cell, for example, before completion of the viral maturation cycle results in the release of incomplete, non-infectious viral particles, thereby treating the viral infection. Destruction of such a cancer cell prevents further metastasis. Where an antibody is used as the ligand, it will often be preferable to administer the antibody and the lytic peptide sequentially, rather than linked to one another. Complement and other responses to the bound antibodies make the cells more susceptible to attack by the lytic peptides.

Lytic Peptides Useful in the Present Invention

It is believed (without wishing to be bound by this theory) that lytic peptides act by disrupting cell membranes. "Resting" eukaryotic cells protect themselves through their ability to repair the resulting membrane damage. By contrast, activated cells (e.g., cells stimulated by GnRH) are unable (or less able) to repair damaged membranes. Because GnRH-activated pituitary cells have a diminished capacity to repair membranes, they are preferentially destroyed by lytic peptides, while adjacent non-activated cells repair their membranes and survive.

Although the embodiments of this invention that have been tested to date have used hecate as the effector lytic peptide, this invention will work with a combination of a ligand with other lytic peptides as well. Many lytic peptides are known in the art and include, for example, those mentioned in the references cited in the following discussion.

Lytic peptides are small, basic peptides. Native lytic peptides appear to be major components of the antimicrobial defense systems of a number of animal species, including those of insects, amphibians, and mammals. They typically comprise 23-39 amino acids, although they can be smaller. They have the potential for forming amphipathic alpha-helices. See Boman et al., "Humoral immunity in *Cecropia pupae*," *Curr. Top. Microbiol. Immunol.* vol. 94/95, pp. 75-91 (1981); Boman et al., "Cell-free immunity in insects," *Annu. Rev. Microbiol.*, vol. 41, pp. 103-126 (1987); Zasloff, "Magainins, a class of antimicrobial peptides from *Xenopus* skin: isolation, characterization of two active forms, and partial DNA sequence of a precursor," *Proc. Natl. Acad. Sci. USA*, vol. 84, pp. 3628-3632 (1987); Ganz et al., "Defensins natural peptide antibiotics of human neutrophils," *J. Clin. Invest.*, vol. 76, pp. 1427-1435 (1985); and Lee et al., "Antibacterial peptides from pig intestine: isolation of a mammalian cecropin," *Proc. Natl. Acad. Sci. USA*, vol. 86, pp. 9159-9162 (1989).

Known amino acid sequences for lytic peptides may be modified to create new peptides that would also be expected to have lytic activity by substitutions of amino acid residues that preserve the amphipathic nature of the peptides (e.g., replacing a polar residue with another polar residue, or a non-polar residue with another non-polar residue, etc.); by substitutions that preserve the charge distribution (e.g., replacing an acidic residue with another acidic residue, or a basic residue with another basic residue, etc.); or by lengthening or shortening the amino acid sequence while preserving its amphipathic character or its charge distribution. Lytic peptides and their sequences are disclosed in Yamada et al., "Production of recombinant sarcotoxin IA in *Bombyx mori* cells," *Biochem. J.*, vol. 272, pp. 633-666 (1990); Taniai et al., "Isolation and nucleotide sequence of cecropin B cDNA clones from the silkworm, *Bombyx mori*," *Biochimica Et Biophysica Acta*, vol. 1132, pp. 203-206 (1992); Boman et al., "Antibacterial and antimalarial properties of peptides that are cecropin-melittin hybrids," *Febs Letters*, vol. 259, pp. 103-106 (1989); Tessier et al., "Enhanced secretion from insect cells of a foreign protein fused to the honeybee melittin signal peptide," *Gene*, vol. 98, pp. 177-183 (1991); Blondelle et al., "Hemolytic and antimicrobial activities of the twenty-four individual omission analogs of melittin," *Biochemistry*, vol. 30, pp. 4671-4678 (1991); Andreu et al., "Shortened cecropin A-melittin hybrids. Significant size reduction retains potent antibiotic activity," *Febs Letters*, vol. 296, pp. 190-194 (1992); Macias et al., "Bactericidal activity of magainin 2: use of lipopolysaccharide mutants," *Can. J. Microbiol.*, vol. 36, pp. 582-584 (1990); Rana et al., "Interactions between magainin-2 and *Salmonella typhimurium* outer membranes: effect of Lipopolysaccharide structure," *Biochemistry*, vol. 30, pp. 5858-5866 (1991); Diamond et al., "Airway epithelial cells are the site of expression of a mammalian antimicrobial peptide gene," *Proc. Natl. Acad. Sci. USA*, vol. 90, pp. 4596 ff (1993); Selsted et al., "Purification, primary structures and antibacterial activities of β-defensins, a new family of antimicrobial peptides from bovine neutrophils," *J. Biol. Chem.*, vol. 268, pp. 6641 ff(1993); Tang et al., "Characterization of the disulfide motif in BNBD-12, an antimicrobial β-defensin peptide from bovine neutrophils," *J. Biol. Chem.*, vol. 268, pp. 6649 ff(1993); Lehrer et al., Blood, vol. 76, pp. 2169-2181 (1990); Ganz et al., *Sem. Resp. Infect. I.*, pp. 107-117 (1986); Kagan et al., *Proc. Natl. Acad. Sci. USA*, vol. 87, pp. 210-214 (1990); Wade et al., *Proc. Natl. Acad. Sci. USA*, vol. 87, pp. 4761-4765 (1990); Romeo et al., *J. Biol. Chem.*, vol. 263, pp. 9573-9575 (1988); Jaynes et al., "Therapeutic Antimicrobial Polypeptides, Their Use and Methods for Preparation," WO 89/00199 (1989); Jaynes, "Lytic Peptides, Use for Growth, Infection and Cancer," WO 90/12866 (1990); Berkowitz, "Prophylaxis and Treatment of Adverse Oral Conditions with Biologically Active Peptides," WO 93/01723 (1993).

Families of naturally-occurring lytic peptides include the cecropins, the defensins, the sarcotoxins, the melittins, and the magainins. Boman and coworkers in Sweden performed the original work on the humoral defense system of *Hyalophora cecropia*, the giant silk moth, to protect itself from bacterial infection. See Hultmark et al., "Insect immunity. Purification of three inducible bactericidal proteins from hemolymph of immunized pupae of *Hyalophora cecropia*," *Eur. J. Biochem.*, vol. 106, pp. 7-16 (1980); and Hultmark et al., "Insect immunity. Isolation and structure of cecropin D. and four minor antibacterial components from *cecropia pupae*," *Eur. J. Biochem.*, vol. 127, pp. 207-217 (1982).

Infection in *H. cecropia* induces the synthesis of specialized proteins capable of disrupting bacterial cell membranes, resulting in lysis and cell death. Among these specialized proteins are those known collectively as cecropins. The principal cecropins—cecropin A, cecropin B, and cecropin D—are small, highly homologous, basic peptides. In collaboration with Merrifield, Boman's group showed that the amino-terminal half of the various cecropins contains a sequence that will form an amphipathic alpha-helix. Andrequ et al., "N-terminal analogues of cecropin A: synthesis, antibacterial activity, and conformational properties," *Biochem.*, vol. 24, pp. 1683-1688 (1985). The carboxy-terminal half of the peptide comprises a hydrophobic tail. See also Boman et al., "Cell-free immunity in *Cecropia*," *Eur. J. Biochem.*, vol. 201, pp. 23-31 (1991).

A cecropin-like peptide has been isolated from porcine intestine. Lee et al., "Antibacterial peptides from pig intestine: isolation of a mammalian cecropin," *Proc. Natl. Acad. Sci. USA*, vol. 86, pp. 9159-9162 (1989).

Cecropin peptides have been observed to kill a number of animal pathogens other than bacteria. See Jaynes et al., "In Vitro Cytocidal Effect of Novel Lytic Peptides on *Plasmodium falciparum* and *Trypanosoma cruzi*," FASEB, 2878-2883 (1988); Arrowood et al., "Hemolytic properties of lytic peptides active against the sporozoites of *Cryptosporidium parvum*," *J. Protozool.*, vol. 38, No. 6, pp. 161 S-163S (1991); and Arrowood et al., "In vitro activities of lytic peptides against the sporozoites of *Cryptosporidium parvum*," *Antimicrob. Agents Chemother.*, vol. 35, pp. 224-227 (1991). However, normal mammalian cells do not appear to be adversely affected by cecropins, even at high concentrations. See Jaynes et al., "In vitro effect of lytic peptides on normal and transformed mammalian cell lines," *Peptide Research*, vol. 2, No. 2, pp. 1-5 (1989); and Reed et al., "Enhanced in vitro growth of murine fibroblast cells and preimplantation embryos cultured in medium supplemented with an amphipathic peptide," *Mol. Reprod. Devel.*, vol. 31, No. 2, pp. 106-113 (1992).

Defensins, originally found in mammals, are small peptides containing six to eight cysteine residues. Ganz et al., "Defensins natural peptide antibiotics of human neutrophils," *J. Clin. Invest.*, vol. 76, pp. 1427-1435 (1985). Extracts from normal human neutrophils contain three defensin peptides: human neutrophil peptides HNP-1, HNP-2, and HNP-3. Defensin peptides have also been described in insects and higher plants. Dimarcq et al., "Insect immunity: expression of the two major inducible antibacterial peptides, defensin and diptericin, in *Phormia terranvae*," *EMBO J.*, vol. 9, pp. 2507-2515 (1990); Fisher et al., *Proc. Natl. Acad. Sci. USA*, vol. 84, pp. 3628-3632 (1987).

Slightly larger peptides called sarcotoxins have been purified from the fleshfly *Sarcophaga peregrina*. Okada et al., "Primary structure of sarcotoxin I, an antibacterial protein induced in the hemolymph of *Sarcophaga peregrina* (flesh fly) larvae," *J. Biol. Chem.*, vol. 260, pp. 7174-7177 (1985). Although highly divergent from the cecropins and defensins, the sarcotoxins presumably have a similar antibiotic function.

Other lytic peptides have been found in amphibians. Gibson and collaborators isolated two peptides from the African clawed frog, *Xenopus laevis*, peptides which they named PGS and Gly$^{10}$Lys$^{22}$PGS. Gibson et al., "Novel peptide fragments originating from PGL$_a$ and the caervlein and xenopsin precursors from *Xenopus laevis*," *J. Biol. Chem.*, vol. 261, pp. 5341-5349 (1986); and Givannini et al., "Biosynthesis and degradation of peptides derived from *Xenopus laevis* prohormones," *Biochem. J.*, vol. 243, pp. 113-120 (1987). Zasloff showed that the *Xenopus*-derived peptides have antimicrobial activity, and renamed them magainins. Zasloff, "Magainins, a class of antimicrobial peptides from *Xenopus* skin: isolation, characterization of two active forms, and partial DNA sequence of a precursor," *Proc. Natl. Acad. Sci. USA*, vol. 84, pp. 3628-3632 (1987).

Synthesis of nonhomologous analogs of different classes of lytic peptides has been reported to reveal that a positively charged, amphipathic sequence containing at least 20 amino acids appeared to be a requirement for lytic activity in some classes of peptides. Shiba et al., "Structure-activity relationship of Lepidopteran, a self-defense peptide of *Bombyx more*," *Tetrahedron*, vol. 44, No. 3, pp. 787-803 (1988). Other work has shown that smaller peptides can also be lytic. See McLaughlin et al., cited below.

Cecropins have been shown to target pathogens or compromised cells selectively, without affecting normal host cells. The synthetic lytic peptide known as S-1 (or Shiva 1) has been shown to destroy intracellular *Brucella abortus*-, *Trypanosoma cruzi*-, *Cryptosporidium parvum*-, and infectious bovine herpes virus I (IBR)-infected host cells, with little or no toxic effects on noninfected mammalian cells. See Jaynes et al., "In vitro effect of lytic peptides on normal and transformed mammalian cell lines," *Peptide Research*, vol. 2, No. 2, pp. 1-5 (1989); Wood et al., "Toxicity of a Novel Antimicrobial Agent to Cattle and Hamster cells In vitro," *Proc. Ann. Amer. Soc. Anim. Sci.*, Utah State University, Logan, Utah. *J. Anim. Sci.* (Suppl. 1), vol. 65, p. 380 (1987); Arrowood et al., "Hemolytic properties of lytic peptides active against the sporozoites of *Cryptosporidium parvum*," *J. Protozool.*, vol. 38, No. 6, pp. 161S-163S (1991); Arrowood et al., "In vitro activities of lytic peptides against the sporozoites of *Cryptosporidium parvum*," *Antimicrob. Agents Chemother.*, vol. 35, pp. 224-227 (1991); and Reed et al., "Enhanced in vitro growth of murine fibroblast cells and preimplantation embryos cultured in medium supplemented with an amphipathic peptide," *Mol. Reprod. Devel.*, vol. 31, No. 2, pp. 106-113 (1992).

Morvan et al., "In vitro activity of the antimicrobial peptide magainin 1 against *Bonamia ostreae*, the intrahemocytic parasite of the flat oyster *Ostrea edulis*," *Mol. Mar. Biol.*, vol. 3, pp. 327-333 (1994) reports the in vitro use of a magainin to selectively reduce the viability of the parasite *Bonamia ostreae* at doses that did not affect cells of the flat oyster *Ostrea edulis*.

Also of interest are the synthetic peptides disclosed in the following pending patent applications, peptides that have lytic activity with as few as 10-14 amino acid residues: McLaughlin et al., "Amphipathic Peptides," U.S. patent application Ser. No. 08/681,075, filed Jul. 22, 1996; and Mark L. McLaughlin et al., "Short Amphipathic Peptides with Activity against Bacteria and Intracellular Pathogens," U.S. patent application Ser. No. 08/796,123, filed Feb. 6, 1997.

Lytic peptides such as are known generally in the art may be used in practicing the present inventions. Selective toxicity to ligand-activated cells is desirable, especially when the ligand and peptide are administered separately. Selective toxicity is less important when the ligand and peptide are linked to one another, because in that case the peptide is effectively concentrated in the immediate vicinity of cells having receptors for the ligand.

Examples of such peptides are those designated D1A21 (SEQ. ID NO. 5), D2A21 (SEQ. ID NO. 6), D5C (SEQ. ID NO. 7), and D5C1 (SEQ. ID NO. 8). These peptides and other lytic peptides suitable for use in the present invention are disclosed in Jaynes, "Methods for the Design of Amphipathic Peptides Having Enhanced Biological Activities," U.S. provisional patent application Ser. No. 60/027,628, filed Oct. 4, 1996. In trials to date using these peptides alone (i.e., one of these four peptides without an associated ligand), in vitro $LD_{50}$ values against human prostate cancer cell lines have ranged from about 0.57 μM to about 1.61 μM. In trials to date using D2A21 alone (i.e., without an associated ligand) $LD_{50}$ values against human breast, bladder, colon, cervix, lung, colon, and skin cancer cell lines have ranged from about 0.28 μM to about 3.1 μM. For comparison, $LD_{50}$ has been measured to be greater than 100 μM for each of D2A21, D5C, and D5C1 for each of the following types of normal, non-cancerous human cells: endothelial cells, fibroblasts, enteric cells, and keratinocytes. For D2A21, $LD_{50}$ has been measured to be about 100 μM for human peripheral blood monocytes, and to be greater than 100 μM for human peripheral blood T-cells.

Other GnRH analogs may be conjugated with a lytic peptide in accordance with this invention. Among the analogs that may be used as part of such a conjugate is I-LHRH-III (or I-GnRH-III), SEQ. ID NO. 16. This peptide has been reported to suppress growth of several cancer cells. See I. Mezö et al., "Synthesis of Gonadotropin-Releasing Hormone III Analogs. Structure-Antitumor Activity Relationships," *J. Med. Chem.* vol. 40, pp. 3353-3358 (1997). The same I-LHRH-III selectively causes the release of FSH. See W. Yu et al., "A hypothalamic follicle-stimulating hormone-releasing decapeptide in the rat," *Proc. Natl. Acad. Sci USA*, vol. 94, pp. 9499-9503 (1997); and U.S. patent application Ser. No. 08/869,153, filed Jun. 4, 1997. Lytic peptide conjugates of I-LHRH-III will be useful as contraceptives, and in the treatment of cancers such as prostate cancers. Agonists of I-LHRH-III, such as are disclosed in U.S. patent application Ser. No. 08/869,153, may be used as well.

Miscellaneous

As used in the Claims, an "effective amount" of a composition is an amount sufficient to selectively kill the targeted cells in a background population of non-targeted cells. Where appropriate in context, an "effective amount" of a composition is also an amount that is sufficient to induce long-term contraception or sterility in an animal. Where appropriate in context, an "effective amount" of GnRH or I-LHRH-III is an amount sufficient to temporarily restore fertility in an animal that has been made sterile by destruction of gonadotropic cells. As used in the Claims, the term "animal" is intended to include both human and non-human metazoans.

The complete disclosures of all references cited in this specification are hereby incorporated by reference; as are the full disclosures of U.S. provisional application 60/041,009, filed Mar. 27, 1997; U.S. provisional application 60/057,456, filed Sep. 3, 1997; and of U.S. non-provisional application Ser. No. 08/869,153, filed Jun. 4, 1997. In the event of an otherwise irreconcilable conflict, however, the present specification shall control.

What is claimed is:

1. A method for killing or inhibiting the growth of a gonadotropin-releasing hormone, lamprey III luteinizing hormone releasing hormone (1-LHRH-III), β-subunit of luteinizing hormone (bLH), estrogen, testosterone, luteinizing hormone, chorionic gonadatropin, follicle stimulating hormone, melanocyte stimulating hormone, estradiol, dopamine, or somatostatin receptor expressing prostate, breast, ovarian, pituitary or endometrial tumor cell in a mammal, comprising administering to the mammal an effective amount of a gonadotropin-releasing hormone, 1-LHRH-III, bLH, estrogen, testosterone, luteinizing hormone, chorionic gonadatropin, follicle stimulating hormone, melanocyte stimulating hormone, estradiol, dopamine, somatostatin, or an analog of these hormones that binds to the receptor expressing prostate, breast, ovarian, pituitary or endometrial tumor cell, and an effective amount of a lytic peptide, wherein said ligand is linked to said lytic peptide, and wherein said lytic peptide consists of 10 to 39 amino acid residues, is basic, and forms an amphipathic alpha helix.

2. A method as recited in claim 1, wherein the cell is part of a pituitary adenoma, and wherein the hormone comprises gonadotropin-releasing hormone, or lamprey III luteinizing hormone releasing hormone (1-LHRH-III).

3. A method as recited in claim 1, wherein the cell is part of a breast cancer, and wherein the hormone comprises gonadotropin-releasing hormone or 1-LHRH-III.

4. A method as recited in claim 1, wherein the cell is part of an ovarian cancer, and wherein the hormone comprises gonadotropin-releasing hormone, 1-LHRH-III, or β-subunit of luteinizing hormone (bLH).

5. A method as recited in claim 1, wherein the cell is part of a prostate cancer, and wherein the hormone comprises gonadotropin-releasing hormone or 1-LHRH-III.

6. A method as recited in claim 1, wherein the cell is part of an ovarian cancer, and wherein the hormone comprises 1-LHRH-III.

7. A method as recited in claim 1, wherein the cell is part of a prostatic cancer, and wherein the hormone comprises 1-LHRH-III.

8. A method as recited in claim 1, wherein the cell is part of a breast cancer, and wherein the ligate hormone comprises 1-LHRH-III.

9. A method as recited in claim 1, wherein the cell is part of an endometrial cancer, and wherein the hormone comprises 1-LHRH-III.

10. A method as recited in claim 1, wherein the cell is part of a testicular cancer, and wherein the hormone comprises gonadotropin-releasing hormone, 1-LHRH-III, or bLH.

11. A method as recited in claim 1, wherein said hormone or hormone analog is bonded directly to said lytic peptide.

12. A method as recited in claim 1, wherein said lytic peptide is selected from the group consisting of a cecropin peptide, a melittin peptide, a defensin peptide, a magainin peptide, a sarcotoxin peptide, and analogs of said peptides.

13. A method as recited in claim 1, wherein said lytic peptide comprises hecate.

14. A method as recited in claim 1, wherein said ligand hormone, hormone analog, or said lytic peptide, or both comprise D-conformation amino acid residues.

15. A method for killing or inhibiting the growth of a gonadotropin-releasing hormone, lamprey III luteinizing hormone releasing hormone (1-LHRH-III), β-subunit of luteinizing hormone (bLH), estrogen, testosterone, luteinizing hormone, chorionic gonadatropin, follicle stimulating hormone, melanocyte stimulating hormone, estradiol, dopamine, or somatostatin hormone receptor expressing tumor cell in a mammal, comprising administering to the mammal an effective amount of a hormone selected from the group consisting of gonadotropin-releasing hormone, 1-LHRH-III, bLH, estrogen, testosterone, luteinizing hormone, chorionic gonadatropin, follicle stimulating hormone, melanocyte stimulating hormone, estradiol, dopamine, somatostatin, and analogs of these hormones, and a lytic peptide domain, wherein said hormone or hormone analog is linked to said lytic peptide domain, and wherein said lytic peptide domain consists of 10 to 39 amino acid residues, is basic, and forms an amphipathic alpha helix.

16. A method as recited in claim 15, wherein said hormone or hormone analog is bonded directly to said lytic peptide domain.

17. A method as recited in claim 15, wherein said lytic peptide domain is selected from the group consisting of a cecropin peptide, a melittin peptide, a defensin peptide, a magainin peptide, a sarcotoxin peptide, and analogs of said peptides.

18. A method as recited in claim 15, wherein said lytic peptide domain comprises hecate.

19. A method as recited in claim 15, wherein said hormone, hormone analog, or said lytic peptide domain, or both comprise D-conformation amino acid residues.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (ix) FEATURE:
      (A) NAME/KEY: Peptide
      (B) LOCATION: 1..10
      (D) OTHER INFORMATION: /note= "Xaa in position 1 denotes
         pyro-glutamic acid. This sequence is GnRH."

(xi) SEQUENCE DESCRIPTION: SEQ ID NO: 1:

Xaa His Trp Ser Tyr Gly Leu Arg Pro Gly
1              5                   10

(2) INFORMATION FOR SEQ ID NO: 2:

(i) SEQUENCE CHARACTERISTICS:
            (A) LENGTH: 23 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..23
            (D) OTHER INFORMATION: /note= "This sequence is hecate."

(xi) SEQUENCE DESCRIPTION: SEQ ID NO: 2:

Phe Ala Leu Ala Leu Lys Ala Leu Lys Lys Ala Leu Lys Lys Leu Lys
1               5                   10                  15

Lys Ala Leu Lys Lys Ala Leu
            20

(2) INFORMATION FOR SEQ ID NO: 3:

(i) SEQUENCE CHARACTERISTICS:
            (A) LENGTH: 33 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..33
            (D) OTHER INFORMATION: /note= "This sequence is a modified
                GnRH/hecate fusion peptide."

(xi) SEQUENCE DESCRIPTION: SEQ ID NO: 3:

Gln His Trp Ser Tyr Gly Leu Arg Pro Gly Phe Ala Leu Ala Leu Lys
1               5                   10                  15

Ala Leu Lys Lys Ala Leu Lys Lys Leu Lys Lys Ala Leu Lys Lys Ala
            20                  25                  30

Leu (2) INFORMATION FOR SEQ ID NO: 4:

(i) SEQUENCE CHARACTERISTICS:
            (A) LENGTH: 33 amino acids
            (B) TYPE: amino acid
            (D) TOPOLOGY: linear (ii) MOLECULE TYPE: peptide (ix) FEATURE:
            (A) NAME/KEY: Peptide
            (B) LOCATION: 1..33
            (D) OTHER INFORMATION: /note= "This sequence is a
                hecate/modified GnRH fusion peptide."

(xi) SEQUENCE DESCRIPTION: SEQ ID NO: 4:

Phe Ala Leu Ala Leu Lys Ala Leu Lys Lys Ala Leu Lys Lys Leu Lys
1               5                   10                  15

Lys Ala Leu Lys Lys Ala Leu Gln His Trp Ser Tyr Gly Leu Arg Pro
            20                  25                  30

Gly (2) INFORMATION FOR SEQ ID NO: 5:

(i) SEQUENCE CHARACTERISTICS:
            (A) LENGTH: 23 amino acids
            (B) TYPE: amino acid
            (D) TOPOLOGY: linear (ii) MOLECULE TYPE: peptide (ix) FEATURE:
        (A) NAME/KEY: Peptide
        (B) LOCATION: 1..23
        (D) OTHER INFORMATION: /note= "This sequence is D1A21."

(xi) SEQUENCE DESCRIPTION: SEQ ID NO: 5:

Phe Ala Phe Ala Phe Lys Ala Phe Lys Lys Ala Phe Lys Lys Phe Lys
1               5                   10                  15

Lys Ala Phe Lys Lys Ala Phe
            20

(2) INFORMATION FOR SEQ ID NO: 6:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..23
        (D) OTHER INFORMATION: /note= "This sequence is D2A21."

(xi) SEQUENCE DESCRIPTION: SEQ ID NO: 6:

Phe Ala Lys Lys Phe Ala Lys Lys Phe Lys Lys Phe Ala Lys Lys Phe
1               5                   10                  15

Ala Lys Phe Ala Phe Ala Phe
            20

(2) INFORMATION FOR SEQ ID NO: 7:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..27
        (D) OTHER INFORMATION: /note= "This sequence is D5C."

(xi) SEQUENCE DESCRIPTION: SEQ ID NO: 7:

Lys Arg Lys Arg Ala Val Lys Arg Val Gly Arg Arg Leu Lys Lys Leu
1               5                   10                  15

Ala Arg Lys Ile Ala Arg Leu Gly Val Ala Phe
            20                  25

(2) INFORMATION FOR SEQ ID NO: 8:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..37
        (D) OTHER INFORMATION: /note= "This sequence is D5C1."

(xi) SEQUENCE DESCRIPTION: SEQ ID NO: 8:

Lys Arg Lys Arg Ala Val Lys Arg Val Gly Arg Arg Leu Lys Lys Leu
1               5                   10                  15

```
Ala Arg Lys Ile Ala Arg Leu Gly Val Ala Lys Leu Ala Gly Leu Arg
            20                  25                  30

Ala Val Leu Lys Phe
        35

(2) INFORMATION FOR SEQ ID NO: 9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "This sequence is a modified
             GnRH."

(xi) SEQUENCE DESCRIPTION: SEQ ID NO: 9:

Gln His Trp Ser Tyr Gly Leu Arg Pro Gly
1               5                   10

(2) INFORMATION FOR SEQ ID NO: 10:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /note= "This sequence is a modified
             alpha-MSH."

(xi) SEQUENCE DESCRIPTION: SEQ ID NO: 10:

Ser Tyr Cys Met Glu His Phe Arg Trp Asn Lys Pro Val
1               5                   10

(2) INFORMATION FOR SEQ ID NO: 11:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..15
        (D) OTHER INFORMATION: /note= "This sequence is bLH."

(xi) SEQUENCE DESCRIPTION: SEQ ID NO: 11:

Ser Tyr Ala Val Ala Leu Ser Cys Gln Cys Ala Leu Cys Arg Arg
1               5                   10                  15

(2) INFORMATION FOR SEQ ID NO: 12:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (ix) FEATURE:
```

(A) NAME/KEY: Peptide
        (B) LOCATION: 1..38
        (D) OTHER INFORMATION: /note= "This sequence is a
            hecate-blH fusion peptide."

(xi) SEQUENCE DESCRIPTION: SEQ ID NO: 12:

Phe Ala Leu Ala Leu Lys Ala Leu Lys Lys Ala Leu Lys Lys Leu Lys
1               5                   10                  15

Lys Ala Leu Lys Lys Ala Leu Ser Tyr Ala Val Ala Leu Ser Cys Gln
            20                  25                  30

Cys Ala Leu Cys Arg Arg
            35

(2) INFORMATION FOR SEQ ID NO: 13:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "Xaa in position 1 denotes
            pyro-glutamic acid.  Xaa in position 6 denotes
            D-lysine.  This sequence is D-Lys-6 GnRH."

(xi) SEQUENCE DESCRIPTION: SEQ ID NO: 13:

Xaa His Trp Ser Tyr Xaa Leu Arg Pro Gly
1               5                   10

(2) INFORMATION FOR SEQ ID NO: 14:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /note= "Xaa in position 1 denotes
            pyro-glutamic acid.  Xaa in position 6 denotes
            acyl-D-lysine."

(xi) SEQUENCE DESCRIPTION: SEQ ID NO: 14:

Xaa His Trp Ser Tyr Xaa Leu Arg Pro Gly
1               5                   10

(2) INFORMATION FOR SEQ ID NO: 15:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..33
        (D) OTHER INFORMATION: /note= "Xaa in position 1 denotes
            pyro-glutamic acid.  This sequence is an
            l-LHRH-III/hecate fusion peptide."

(xi) SEQUENCE DESCRIPTION: SEQ ID NO: 15:

Xaa His Trp Ser His Asp Trp Lys Pro Gly Phe Ala Leu Ala Leu Lys

```
                1               5              10              15
Ala Leu Lys Lys Ala Leu Lys Lys Leu Lys Lys Ala Leu Lys Lys Ala
               20              25              30

Leu (2) INFORMATION FOR SEQ ID NO: 16:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: Peptide
         (B) LOCATION: 1..10
         (D) OTHER INFORMATION: /note= "Xaa in position 1 denotes
             pyro-glutamic acid.  This sequence is l-LHRH-III."

(xi) SEQUENCE DESCRIPTION: SEQ ID NO: 16:

Xaa His Trp Ser His Asp Trp Lys Pro Gly
1               5                     10

(2) INFORMATION FOR SEQ ID NO: 17:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: Peptide
         (B) LOCATION: 1..10
         (D) OTHER INFORMATION: /note= "Xaa in position 1 denotes
             pyro-glutamic acid.  This sequence is chicken I
             GnRH."

(xi) SEQUENCE DESCRIPTION: SEQ ID NO: 17:

Xaa His Trp Ser Tyr Gly Leu Gln Pro Gly
1               5                     10

(2) INFORMATION FOR SEQ ID NO: 18:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
         (A) NAME/KEY: Peptide
         (B) LOCATION: 1..10
         (D) OTHER INFORMATION: /note= "Xaa in position 1 denotes
             pyro-glutamic acid.  This sequence is chicken II
             GnRH."

(xi) SEQUENCE DESCRIPTION: SEQ ID NO: 18:

Xaa His Trp Ser His Gly Trp Tyr Pro Gly
1               5                     10
```